US011313828B2

(12) United States Patent
Kang et al.

(10) Patent No.: US 11,313,828 B2
(45) Date of Patent: Apr. 26, 2022

(54) ULTRA-HIGHLY SENSITIVE ELECTROCHEMICAL BIOSENSOR USING BEADS AND METHOD FOR MANUFACTURING THE SAME

(71) Applicant: KOREA INSTITUTE OF SCIENCE AND TECHNOLOGY, Seoul (KR)

(72) Inventors: Ji Yoon Kang, Seoul (KR); Kyeong-Sik Shin, Seoul (KR); Jae-hoon Ji, Seoul (KR); Kyoseon Hwang, Seoul (KR); Tae Song Kim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 143 days.

(21) Appl. No.: 14/994,389

(22) Filed: Jan. 13, 2016

(65) Prior Publication Data

US 2017/0131233 A1 May 11, 2017

(30) Foreign Application Priority Data

Nov. 9, 2015 (KR) .................. 10-2015-0156981

(51) Int. Cl.
*G01N 27/416* (2006.01)
*G01N 27/327* (2006.01)
*G01N 33/543* (2006.01)

(52) U.S. Cl.
CPC ..... *G01N 27/4166* (2013.01); *G01N 27/3275* (2013.01); *G01N 33/5438* (2013.01)

(58) Field of Classification Search
CPC ..... G01N 33/48707; G01N 27/406–41; G01N 33/0004–0075; B03C 5/026;
(Continued)

(56) References Cited

U.S. PATENT DOCUMENTS 7,645,615 B1 * 1/2010 Fritsch ................ B01F 13/0077
436/518
10,093,975 B2 * 10/2018 Esfandyarpour ......... B03C 5/02
(Continued)

FOREIGN PATENT DOCUMENTS

| JP | 2015-500640 A | 1/2015 | |
| KR | 10-2009-0020014 A | 2/2009 | |
| WO | WO-2014073195 A1 * | 5/2014 | ....... G01N 33/48728 |

OTHER PUBLICATIONS

Date et al. (Y Date, S Takano, H Shiku, K Ino, T Ito-Sasaki, M Yokoo, H Abe, T Matsue, Monitoring oxygen consumption of single mouse embryos using an integrated electrochemical microdevice, Biosensors and Bioelectronics 30 (2011) 100-106). (Year: 2011).*
(Continued)

*Primary Examiner* — Joshua L Allen
(74) *Attorney, Agent, or Firm* — NSIP Law (57) ABSTRACT

The biosensor includes a substrate, an electrode pattern positioned on the substrate, a passivation layer which is formed with a plurality of holes spaced apart from each other, and a bead positioned at one or more holes among the plurality of holes, and to which an antibody is attached, the electrode pattern includes a first electrode pattern part and a second electrode pattern part spaced apart from the first electrode pattern part, which has a same height as a height of the first electrode pattern part, and forms an electric field with the first electrode pattern part.

10 Claims, 10 Drawing Sheets

(58) Field of Classification Search
CPC . B03C 5/005; B03C 2201/26; B03C 2201/18; B03C 2201/20

See application file for complete search history.

(56) References Cited

U.S. PATENT DOCUMENTS

| | | | | |
|---|---|---|---|---|
| 2005/0112544 | A1* | 5/2005 | Xu | C12M 23/12 435/4 |
| 2005/0175981 | A1* | 8/2005 | Voldman | B03C 5/005 435/4 |
| 2009/0093376 | A1* | 4/2009 | Wo | B03C 5/026 506/14 |
| 2009/0178922 | A1* | 7/2009 | Nakatani | G01N 33/48728 204/403.01 |
| 2009/0202985 | A1* | 8/2009 | Gulak | C12Q 1/18 435/5 |
| 2010/0311608 | A1* | 12/2010 | Osada | B03C 1/01 506/9 |
| 2012/0064567 | A1* | 3/2012 | Stakenborg | B03C 5/005 435/39 |
| 2013/0034880 | A1* | 2/2013 | Oldham | B01L 3/502738 435/91.5 |
| 2014/0227679 | A1* | 8/2014 | Lee | B03C 1/01 435/5 |
| 2014/0329699 | A1* | 11/2014 | Esfandyarpour | G01N 27/3278 506/6 |
| 2015/0260675 | A1* | 9/2015 | Nakatani | G01N 33/48728 204/403.01 |
| 2017/0023512 | A1* | 1/2017 | Cummins | G01N 33/5438 |
| 2017/0248541 | A1* | 8/2017 | Liu | G01N 27/4074 |

OTHER PUBLICATIONS

Choi et al. (J-W Choi, KW Oh, JH Thomas, WR Heineman, HB Halsall, JH Nevin, AJ Helmicki, T Henderson, CH Ahn, An integrated microfluidic biochemical detection system for protein analysis with magnetic bead-based sampling capabilities, Lab Chip 2 (2002) 27-30). (Year: 2002).*

Kyeong-Sik Shin, et al., "Novel Detection Platform for Alzheimer's Amyloid-Beta Using Magnetic Beads in Electrochemical Impedance Spectroscopy", MEMS 2015, Estoril, Portugal, Jan. 18-22, 2015 (4 pages in English).

Kyeong-Sik Shin, et al., "Impedance-based Label Free detection for Alzheimer' Amyloid beta" MEMS Korea 2015, Apr. 2-4, 2015 (2 pages in Korean with English abstract).

Kyeong-Sik Shin, et al., "Novel Label Free Detection Platform with Ultra-High Sensitivity Using Magnetic Beads for Prostate-Specific Antigen (PSA)", International Conference on Miniaturized Systems for Chemistry and Life Sciences, Oct. 25-29, 2015, Gyeongju, Republic of Korea (3 pages in English).

Korean Office Action dated Oct. 30, 2016 in counterpart Korean Application No. 10-2015-0156981. (5 pages in Korean).

* cited by examiner

ULTRA-HIGHLY SENSITIVE ELECTROCHEMICAL BIOSENSOR USING BEADS AND METHOD FOR MANUFACTURING THE SAME

CROSS-REFERENCE TO RELATED APPLICATION

This application claims priority to and the benefit of Korean Patent Application No. 10-2015-0156981 filed in the Korean Intellectual Property Office on Nov. 9, 2015, the entire contents of which are incorporated herein by reference.

BACKGROUND OF THE INVENTION (a) Field of the Invention

A ultra-highly sensitive electrochemical biosensor using beads, and a method for manufacturing the same are provided.

(b) Description of the Related Art

A highly sensitive biosensor is advantageously applicable to an early diagnosis and the like of various diseases, and as a result, many research and development therefor have been conducted. It is expected that the highly sensitive biosensor replaces an optical detecting method, such as an enzyme-linked immunosorbent assay (ELISA) widely used in the related art.

A currently used highly sensitive biosensors may be classified into a field effective transistor (FET) sensor and an electrochemical sensor. Here, as the FET, a nanowire FET or an ion-selective field effective transistor (ISFET) is used. The electrochemical sensor is easily manufactured and used, but has a problem in that a detection limit, at which a low concentration may be measured, is merely several tens of pg/ml. In order to overcome the limit, sensitivity is improved by tagging gold nano particles (AuNP) and the like to an antigen. Further, in order to detect a bio-material by the electrochemical sensor, a method of fixing an antibody to a surface of an electrode and detecting an antigen is used. This method has a disadvantage in that after the electrochemical sensor is used once, it is difficult to reuse the electrochemical sensor.

The above information disclosed in this Background section is only for enhancement of understanding of the background of the invention and therefore it may contain information that does not form the prior art that is already known in this country to a person of ordinary skill in the art.

SUMMARY OF THE INVENTION

An exemplary embodiment relates to an electrochemical biosensor, which is capable of detecting a concentration of antigens even at extremely low level by reacting the antigen to a magnetic bead, to which an antibody is fixed, and a method for manufacturing the same.

An exemplary embodiment provides a biosensor, which is capable of quantifying a concentration of antigens up to an extremely low level after capturing the antigen with beads, to which an antibody is fixed.

An exemplary embodiment provides a method for manufacturing the biosensor.

An exemplary embodiment provides a biosensor, including: i) a substrate; ii) an electrode pattern positioned on the substrate; iii) a passivation layer positioned on the electrode pattern, the passivation layer covers the substrate, and includes a plurality of holes spaced apart from each other; and iv) a bead positioned at one or more holes among the plurality of holes, the bead being attached to an antibody. The electrode pattern may include: i) a first electrode pattern part; and ii) a second electrode pattern part spaced apart from the first electrode pattern part, the second electrode pattern part has a same height as a height of the first electrode pattern part, and forms an electric field with the first electrode pattern part. The first electrode pattern part includes a first exposed electrode exposed to the outside through the hole, the second electrode pattern part includes a second exposed electrode exposed to the outside through the hole, and the bead is in contact with the first exposed electrode and the second exposed electrode.

A portion of the passivation layer may be in direct contact with the substrate, and a height of the portion of the passivation layer may be from about ⅔ to about 5 times a diameter of the bead. More preferably, a part of the passivation layer may be in direct contact with the substrate, and a height of the part of the passivation layer may be from about 3 to about 20 times the diameter of the bead when the diameter of the bead is about 1 µm or less. The first exposed electrode may have a linear shape, and an end of the first exposed electrode may be in contact with the bead, and the second exposed electrode may have a curved shape surrounding the bead. A voltage may be applied to the first electrode pattern part, and the second electrode pattern part may be grounded.

The biosensor may further include a pair of third exposed electrodes positioned between the first exposed electrode and the second exposed electrode, the pair of third exposed electrodes surround the bead, and form an electric field with the first exposed electrode and the second exposed electrode. The first exposed electrode has a linear shape and the second exposed electrode has a linear shape, and the first exposed electrode and the second exposed electrode are spaced apart from each other and are extended in the same direction. One or more third exposed electrodes among the pair of third exposed electrodes may include: i) a first part of the third exposed electrode extended in a direction parallel to a direction in which the first exposed electrode is extended; and ii) a pair of second part of the third exposed electrode extended from both ends of the first part of the third exposed electrode, the pair of second part of the third exposed electrode are extended toward the first exposed electrode and the second exposed electrode, respectively. The pair of second part of the third exposed electrode may be spaced apart from the first exposed electrode and the second exposed electrode. A length of each of the pair of second part of the third exposed electrode may be smaller than a length of the first part of the third exposed electrode part.

The first electrode pattern part may include: i) a first main electrode extended in a first direction; ii) a plurality of first auxiliary electrodes spaced apart from each other, the plurality of the first auxiliary electrodes are connected with the first main electrode, and extended in a second direction; and iii) a plurality of first reaction electrodes connected with the first auxiliary electrodes, respectively, among the plurality of first auxiliary electrodes and extended in the first direction. The second electrode pattern part may include: i) a second main electrode spaced apart from the first main electrode and extended in the first direction; ii) a plurality of second auxiliary electrodes spaced apart from each other, the plurality of second auxiliary electrodes are connected with the second main electrode extended in the second direction, and alternately positioned with the first auxiliary electrodes; and iii) a plurality of second reaction electrodes connected with the second auxiliary electrodes, respectively, among the plurality of second auxiliary electrodes, and extended in the first direction. The first electrode pattern part further includes a plurality of first branched electrodes spaced apart from each other and connected with the plurality of first reaction electrodes, the second electrode pattern part further includes a plurality of second branched electrodes spaced apart from each other and connected with the plurality of second reaction electrodes. One or more first branched electrodes among the plurality of first branched electrodes may include the first exposed electrode, and one or more second branched electrodes among the plurality of second branched electrodes may include the second exposed electrode.

The biosensor may further include a micro channel member covering the passivation layer, in which the micro channel member includes micro injection holes communicated with the plurality of holes. The biosensor may further include a magnetic body positioned under the substrate, the magnetic body is freely movable under the substrate, and the bead may have a magnetic property. The biosensor may further include a third electrode pattern part spaced apart from the second electrode pattern part, the third electrode pattern part has a same height as a height of the second electrode pattern part, and forms an electric field with the first electrode pattern part and the second electrode pattern part, and forms an electric field with the second electrode pattern part. The third electrode pattern part may include the third electrode pattern part includes a third exposed electrode exposed to the outside through the hole, and the bead is in contact with the first exposed electrode, the second exposed electrode, and the third exposed electrode.

An exemplary embodiment provides a method of manufacturing a biosensor, including: i) providing a substrate; ii) providing a conductive layer on the substrate; iii) positioning a first mask layer on the conductive layer, and forming a pattern by exposing and developing the first mask layer; iv) forming an electrode pattern on the conductive layer through the first mask layer formed with the pattern; v) providing a passivation layer covering the substrate and the electrode pattern; vi) positioning a second mask layer on the passivation layer, and forming a plurality of holes by exposing and developing the second mask layer, and then etching the passivation layer; and vii) inserting beads attached with antibodies into the plurality of holes. In the forming of the electrode pattern, openings may be formed in the electrode pattern, the openings may correspond to the holes, and a size of the opening may be smaller than a size of the hole.

The inserting of the beads into the plurality of holes may include: i) positioning a micro channel member formed with micro channels communicated with the plurality of holes and micro injection holes, on the passivation layer; ii) inserting the beads into the plurality of holes through the micro injection holes by injecting the beads into the micro channels; and iii) removing the beads positioned outside the holes by using a buffer solution.

According to the exemplary embodiment, it is possible to simplify an analysis procedure by using an immunity analysis device, and decrease an analysis time. Further, it is possible to efficiently perform the large amount of immunity analysis by utilizing an automation system.

DETAILED DESCRIPTION OF THE EMBODIMENTS

The terminologies used herein are set forth to illustrate a specific exemplary embodiment but not to limit the present invention. It should be noted that, as used in the specification and the appended claims, the singular forms include plural references unless the context clearly dictates otherwise. It will be further understood that the terms "comprises" and/or "comprising," when used in this specification, specify the presence of stated properties, regions, integers, steps, operations, elements, and/or components, but do not preclude the presence or addition of one or more other specific properties, regions, integers, steps, operations, elements, components, and/or groups.

Unless otherwise defined, all terms including technical terms and scientific terms used herein have the same meaning as that generally understood by the person with ordinary skill in the art to which the present invention belongs. The terminologies that are defined in a commonly used dictionary are further interpreted to have meanings that coincide with contents that are disclosed in related technical documents, but not as idealized or overly official meanings unless otherwise defined.

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention.

Figure 1:
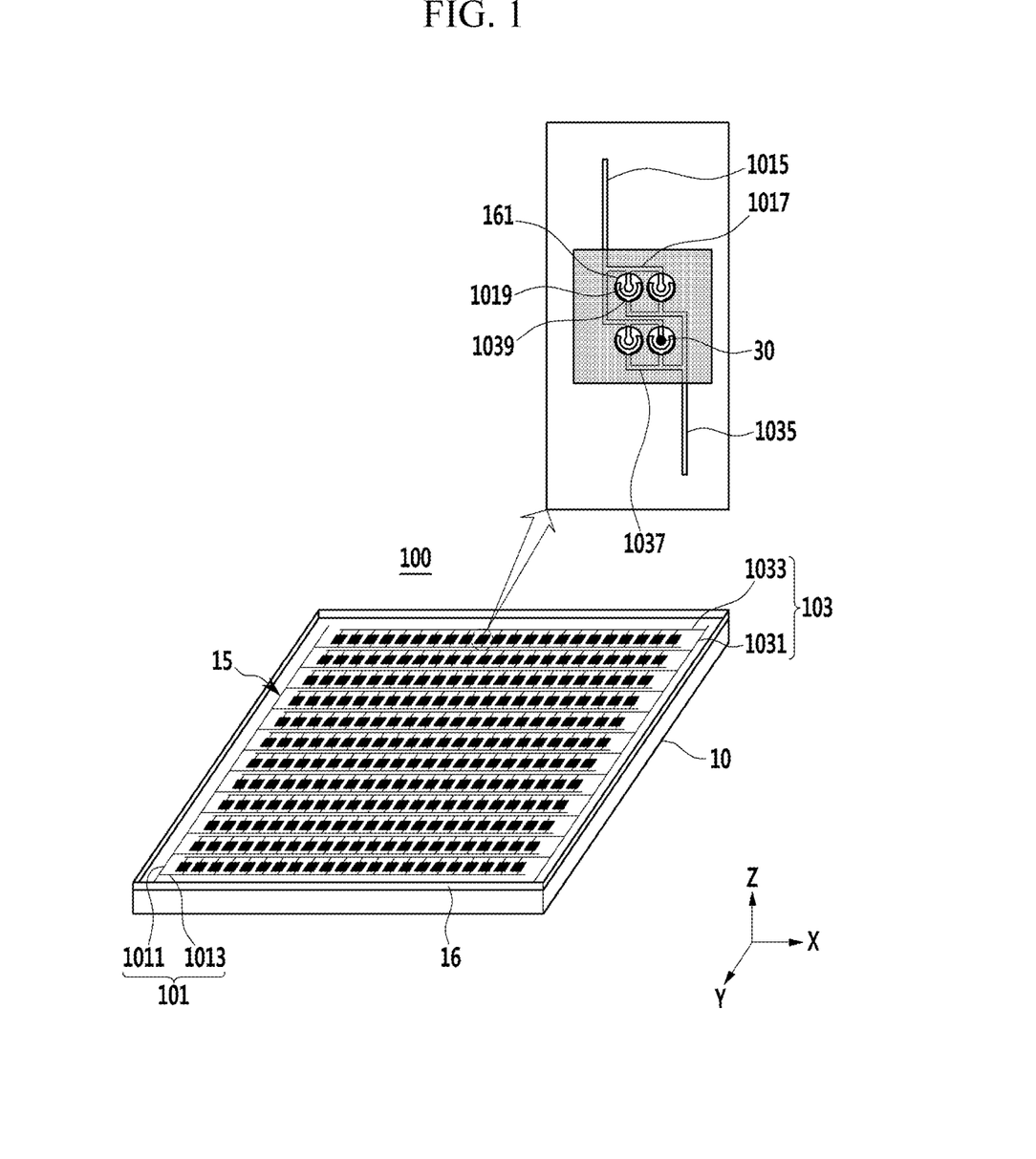
FIG. 1 is a schematic perspective view of a biosensor according to a first exemplary embodiment.

FIG. 1 schematically illustrates a biosensor 100 according to a first exemplary embodiment. FIG. 1 illustrates an enlarged sensing unit, in which beads 30 of the biosensor 100 are positioned. A structure of the biosensor 100 of FIG. 1 is simply for the purpose of illustrating the present invention, and the present invention is not limited thereto. Accordingly, the structure of the biosensor 100 may be modified into another form.

As illustrated in FIG. 1, the biosensor 100 includes a substrate 10, an electrode pattern 15, a passivation layer 16, and the beads 30. In addition, the biosensor 100 may further include other components as necessary.

The substrate 10 is formed of a transparent material, such as glass. Accordingly, it is possible to confirm the beads 30 and holes 161, in which the beads 30 are positioned through the substrate 10. The substrate 10 is formed in a plane shape while having a predetermined thickness to support the electrode pattern 15 and the passivation layer 16.

The electrode pattern 15 is positioned on the substrate 10. The electrode pattern 15 is positioned on the substrate 10 to apply an electric field to the beads 30 by a voltage difference between the electrodes. Accordingly, the biosensor 100 may detect an antigen at an extremely low concentration by measuring impedance according to an electric field reaction with the antigen.

As illustrated in FIG. 1, the electrode pattern 15 includes a first electrode pattern part 101 and a second electrode pattern part 103, which are spaced apart from each other. Here, the first electrode pattern part 101 includes a first main electrode 1011 and first auxiliary electrodes 1013. The first main electrode 1011 is elongated in a first direction parallel to a y-axis. Further, the first auxiliary electrodes 1013 are connected with the first main electrode 1011 and elongated in a second direction, which is parallel to an x-axis and crosses the first direction. Accordingly, it is possible to apply a voltage to the first auxiliary electrodes 1013, which are spaced apart from each other, through the first main electrode 1011, which is electrically connected with an external power supply and receives power.

As illustrated in the enlarged part of FIG. 1, the first electrode pattern 101 further includes a first reaction electrode 1015, first branched electrodes 1017, and first exposed electrodes 1019, which are connected to each other. The first reaction electrode 1015 is connected to the first auxiliary electrodes 1013 and elongated in the y-axis direction. The first branched electrodes 1017 are connected to the first reaction electrode 1015 and elongated in the x-axis direction. The first branched electrodes 1017 are spaced apart from each other and branched from the first reaction electrode 1015. The first branched electrodes 1017 are connected with the first exposed electrodes 1019, which are spaced apart from each other. The first exposed electrodes 1019 are exposed to the outside through the holes 161. The first exposed electrode 1019 is elongated in the y-axis direction.

In the meantime, the second electrode pattern part 103 includes a second main electrode 1031 and second auxiliary electrodes 1033. The second main electrode 1031 is elongated in the y-axis direction. Further, the second auxiliary electrodes 1033 are connected with the second main electrode 1031 and elongated in the x-axis direction, and are alternately positioned with the first auxiliary electrodes 1013. Accordingly, it is possible to apply a voltage to the second auxiliary electrodes 1033, which are spaced apart from each other, through the second main electrode 1031, which is electrically connected with an external power supply and receives power.

As illustrated in the enlarged part of FIG. 1, the second electrode pattern part 103 further includes a second reaction electrode 1035 and second exposed electrodes 1039, which are connected to each other. The second reaction electrode 1035 is connected with the second auxiliary electrodes 1033 and bent. Further, the second exposed electrodes 1039 are exposed to the outside through the holes 161. The second exposed electrode 1039 is formed in a curved shape surrounding the bead 30.

As illustrated in FIG. 1, the bead 30 is in contact with the first exposed electrode 1019 and the second exposed electrode 1039. More particularly, an end portion of the first exposed electrode 1019 formed in a linear shape is in contact with the bead 30. Here, the first exposed electrode 1019 may be a working electrode, and the second exposed electrode 1039 may be a counter electrode. Otherwise, an opposite case may be available. Accordingly, an electric field is formed by a difference in potential between the first exposed electrode 1019 and the second exposed electrode 1039, and different impedance is represented according to the quantity of antigen attached to the beads 30. As a result, the biosensor 100 may detect the minute amount of antigen by measuring the impedance.

The biosensor 100 of FIG. 1 may be used for diagnosis of Alzheimer's disease. Alzheimer's disease is a degenerative brain disease, and causes severe disorders in memory, daily living capability, and behavior according to the progress thereof. Manifestation of Alzheimer's disease means that the brain is already severely damaged, and unfortunately, there is no specific medical treatment for Alzheimer's disease at present. Accordingly, in order to prevent aggravation of symptoms, it is important to diagnose Alzheimer's disease early. Amyloid beta (Aβ) is recognized as a main factor of the generation of Alzheimer's disease. It is known that when Amyloid beta (Aβ) becomes an oligomer, a nervous system is damaged. Accordingly, it is very important to detect an amyloid beta oligomer (AβO) early in order to diagnose Alzheimer's disease.

In general, it is known that Aβ is detected by an enzyme-linked immuno sorbent assay (ELISA), and may be detected by the FET and the electrochemical method. Particularly, the electrochemical method among them has an advantage in that it is easy to manufacture a sensor and high sensor sensitivity and reliability are achieved, but a surface treatment with an antibody and the like needs to be performed on a surface of an electrochemical sensor. A reaction between the antibody, which is fixed by the surface treatment, and an external antigen is represented as a change in transfer resistance, and in order to measure the transfer resistance, it is necessary to do so according to a frequency.

Contrary to this, in the first exemplary, even if the biosensor 100 is not surface treated by using the magnetic beads 30, it is possible to measure the Aβ by the impedance scheme at a fixed frequency. Accordingly, it is possible to accurately diagnose Alzheimer's disease through the biosensor 100. In the meantime, when the bead 30 is made of metal or a synthetic material, it is possible to measure impedance by capturing the beads 30 into the holes 161 through dielectrophoresis (DEP). Hereinafter, a manufacturing process of the biosensor 100 of FIG. 1 will be described in more detail with reference to FIG. 2.

Figure 2:
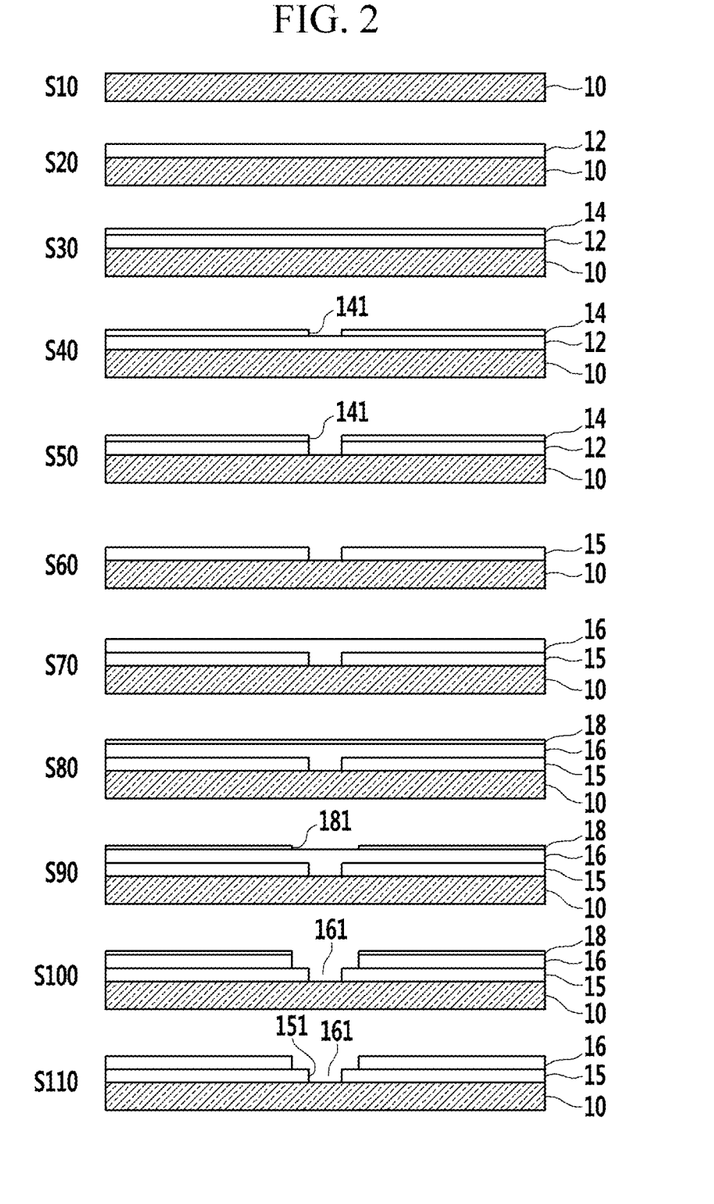
FIG. 2 is a state view illustrating a schematic method for manufacturing the biosensor of FIG. 1.

FIG. 2 schematically illustrates a method for manufacturing the biosensor 100 of FIG. 1 according to an order. The method for manufacturing the biosensor 100 of FIG. 2 is simply for the purpose of illustrating the present invention, and the present invention is not limited thereto. Accordingly, the method for manufacturing the biosensor 100 may also be modified into another form.

First, a substrate 10 is provided in operation S10 of FIG. 2. The substrate 10 may include glass or a plastic material having an optical transmissive property.

Next, in operation S20, a conductive layer 12 is deposited on the substrate 10. A conductive material, such as Ti/Pt, may be used as a material of the conductive layer 12. The substrate 10 is inserted into a chamber (not illustrated), and then conductive layer 12 is provided by using a method, such as physical vapor deposition.

Then, in operation S30, a mask layer 14 is positioned on the conductive layer 12. In a subsequent process, an electrode pattern is formed by using the mask layer 14.

In operation S40, a predetermined electrode pattern is formed by exposing and developing the mask layer 14. As a result, an opening 141 is formed at a portion, which needs to be removed in order to form the electrode pattern 15.

Further, in operation S50, an etchant comes into contact with the conductive layer 12 through the opening 141 of the mask layer 14. As a result, the conductive layer 12, which is positioned at the portion corresponding to the opening 141 is etched and removed, so that the electrode pattern 15 is formed.

Next, in operation S60, the mask layer 14 is removed. Accordingly, it is possible to obtain the electrode pattern 15, in which an unnecessary portion is removed. Depending on a case, the mask layer 14 may not be removed.

In operation S70, a passivation layer 16 covering the substrate 10 and the electrode pattern 15 is provided by a method, such as spin coating. A resin having an electric insulation property and the like may be used as a material of the passivation layer 16.

Then, in operation S80, a mask layer 18 is positioned on the passivation layer 16. The mask layer 18 is used for forming a hole 161 in a subsequent process.

Next, in operation S90, an opening 181 is formed by exposing and developing the mask layer 18 with a predetermined hole pattern.

In operation S100, the passivation layer 16 is etched through the opening 181. As a result, it is possible to form the hole 161, into which a bead is inserted and fixed. Here, an opening 151 formed in the electrode pattern 15 corresponds to the hole 161. A size of the opening 151 is smaller than a size of the hole 161. Accordingly, it is possible to manufacture the hole 161 having a sufficient size such that the bead is inserted and fixed to the hole 161. A diameter of the hole 161 may be about 3 µm to about 5 µm. When the diameter of the hole 161 is excessively small, it is impossible to capture the bead 30. Further, when the diameter of the hole 161 is excessively large and a height of the hole 161 is small, the bead 30 may be easily separated from the hole 161. Accordingly, a diameter of the hole 161 is adjusted to the aforementioned range.

Last, in operation S110, the mask layer 18 is removed. Depending on a case, operation S110 may be omitted. As a result, it is possible to manufacture the biosensor 100 of FIG. 1. The aforementioned contents may be easily understood by those skilled in the art, so that detailed descriptions of contents of each detailed process will be omitted.

Figure 3:
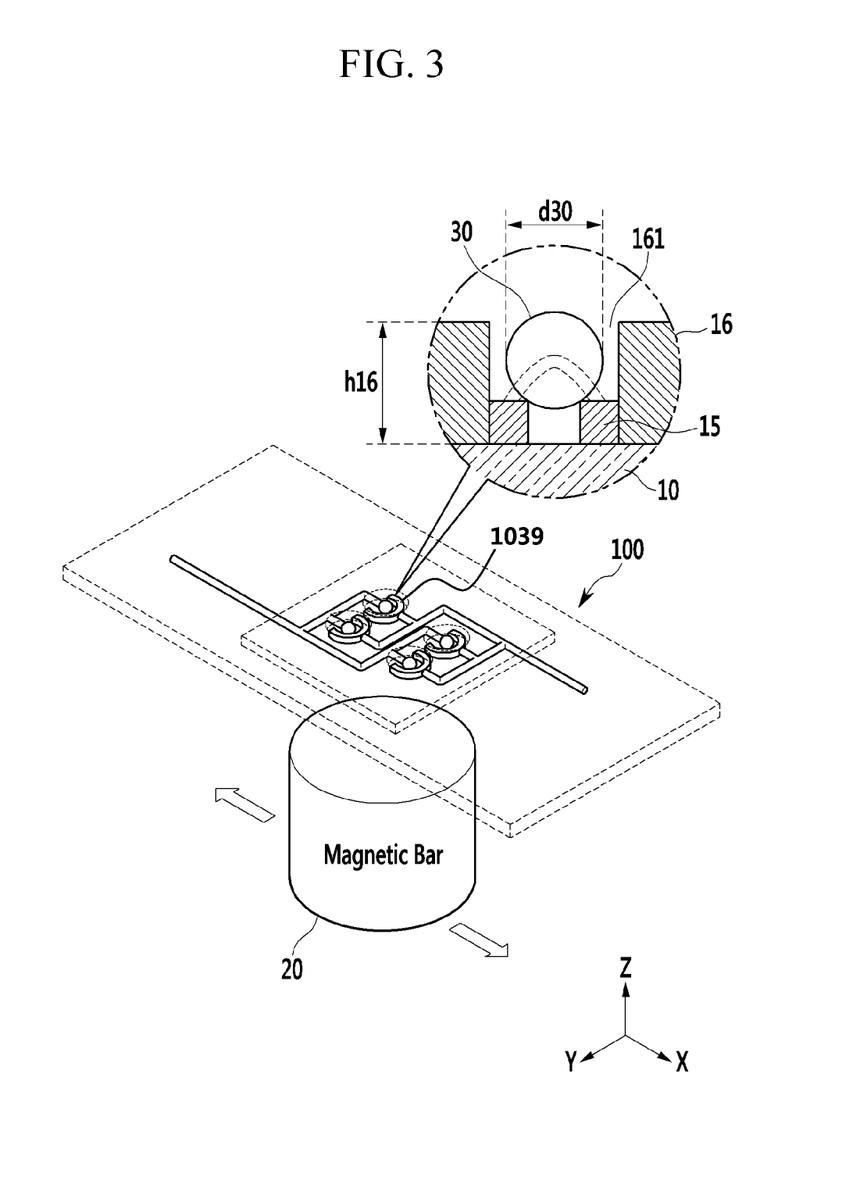
FIG. 3 is a schematic operation state view of the biosensor of FIG. 1.

FIG. 3 schematically illustrates an operation state of the biosensor 100 of FIG. 1. An enlarged circle of FIG. 3 represents a state of a measurement of impedance by applying an electric field by making antigens having different concentrations to the bead 30, to which an antibody is fixed, flow. FIG. 3 illustrates an enlarged part of the biosensor 100 for convenience of description.

As illustrated in FIG. 3, when the beads 30 are provided at the biosensor 100, some of the beads 30 are inserted and fixed to the holes 161, but some other of the beads 30 exist on the passivation layer 16. Accordingly, a magnetic body 20 is positioned at a lower side of the biosensor 100, and when the magnetic body 20 freely moves in an arrow direction in FIG. 3 so as to cover a front surface of the biosensor 100, the beads 30 may be attracted in a −z-axis direction by magnetic force. As a result, the beads 30 may be inserted into and fixed to all of the holes 161. Accordingly, a large amount of beads 30 may be used, so that a concentration of antigens attached to the beads 30 may be quantified as an average. Accordingly, it is possible to extract a concentration of the minute amount of antigens, and it is possible to minimize an antigen concentration measurement error. In this case, the beads 30 may be formed of a material having a magnetic property.

In the meantime, as illustrated in the enlarged circle of FIG. 3, a height h16 of a portion of the passivation layer 16, which is in direct contact with the substrate 10, may be about ⅔ to about 5 times the diameter d30 of the bead 30. When the ratio is excessively small, the bead 30 is excessively exposed to the outside, so that the bead 30 may not be fixed to the hole 161. Further, when the ratio is excessively large, a height of the passivation layer 16 is excessively large, so that it is impossible to manufacture the biosensor 100. Accordingly, the height h16 of the passivation layer 16 may be maintained within the aforementioned range. More preferably, the ratio may be about ⅔ to 3.

The diameter d30 of the bead 30 may be about 1 µm to about 3 µm. The diameter d30 of the bead 30 may be about 1 µm or less, and the hole 161 may collect the plurality of beads 30. In the meantime, when the diameter of the bead 30 is about 1 µm or less, the height h16 of the passivation layer 16 may be about 3 to about 20 times the diameter d30 of the bead 30. That is, when the diameter of the bead 30 is excessively small, it is possible to stably locate the bead 30 within the hole 161 by further increasing the height h16 of the passivation layer 16.

Figure 4:
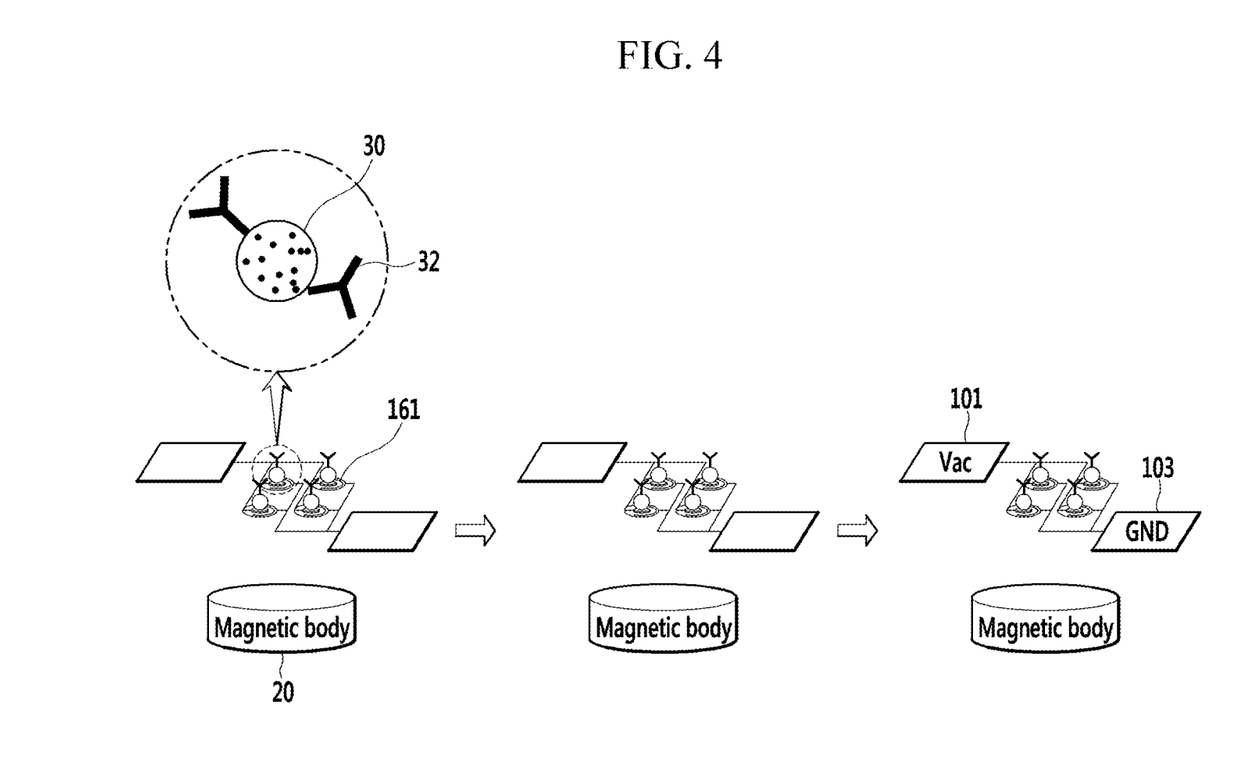
FIG. 4 is a diagram sequentially illustrating a schematic process for measuring a concentration of antigens by using the biosensor of FIG. 1.

FIG. 4 sequentially illustrates a schematic process for measuring a concentration of antigens by using the biosensor of FIG. 1. An enlarged circle of FIG. 4 represents the enlarged bead 30, to which the antigens 32 are fixed. The process for measuring a concentration of antigens by the biosensor 100 of FIG. 4 is simply for the purpose of illustrating the present invention, and the present invention is not limited thereto. Accordingly, the process for measuring a concentration of antigens by the biosensor 100 may be modified into another form.

As illustrated in FIG. 4, the beads 30, to which the antigens 32 are fixed, are moved to be located inside the holes 161 by using the magnetic body 20. As a result, the beads 30 are stably located inside the holes 161. Further, the second electrode pattern part 103 is grounded (GND) while applying a voltage(Vac) to the first electrode pattern part 101, and impedance is measured by causing antigens having different concentrations to flow therein. As a result, impedance is changed according to a concentration of antigens captured by the beads 30, to which antibodies are fixed, while an electric field is formed between the first electrode pattern part 101 and the second electrode pattern part 103, so that it is possible to measure a minute concentration of antigens corresponding to the impedance value. For example, it is possible to measure the concentration of antigens up at about 10 pg/ml or less with high sensitivity.

Figure 5:
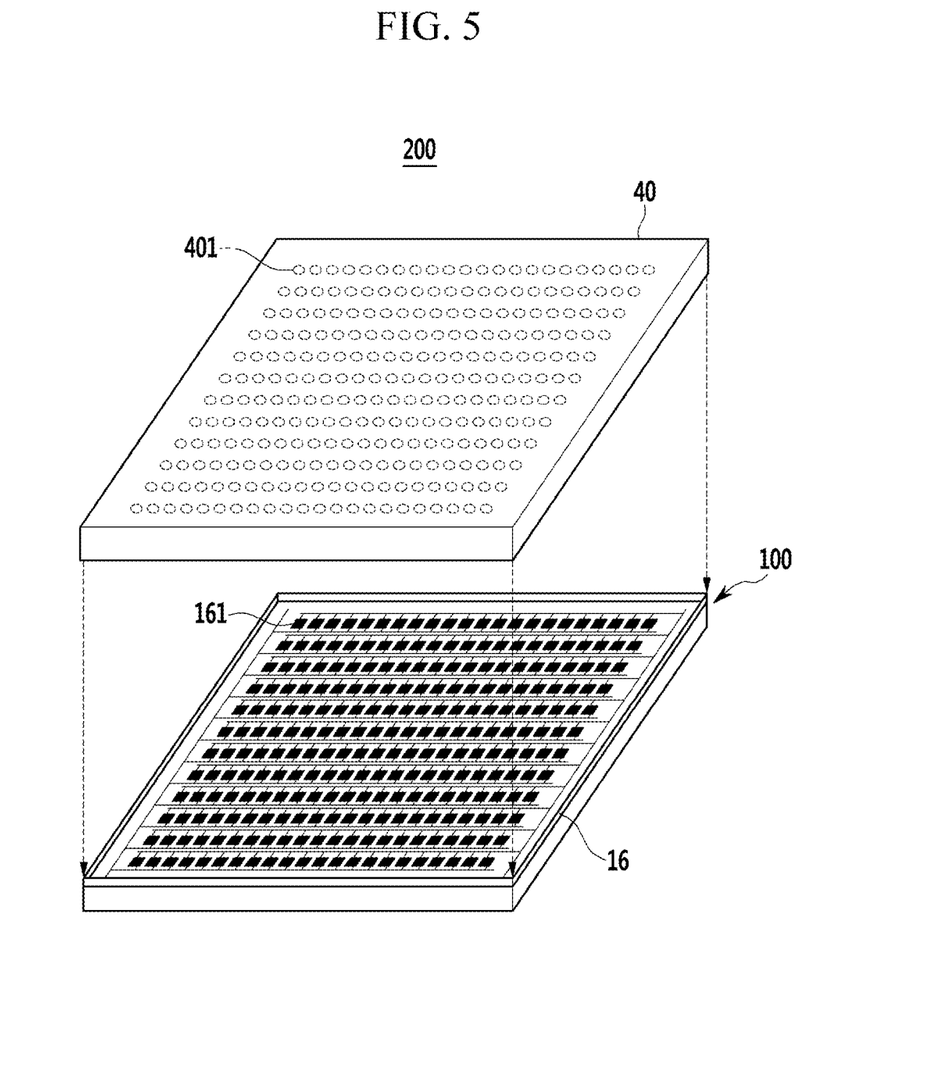
FIG. 5 is a schematic exploded perspective view of a biosensor according to a second exemplary embodiment.

FIG. 5 schematically illustrates an exploded biosensor 200 according to a second exemplary embodiment. A structure of the biosensor 200 of FIG. 5 is similar to that of the biosensor 100 of FIG. 1, so that the same parts are denoted by the same reference numerals, and a detailed description thereof will be omitted.

As illustrated in FIG. 5, the biosensor 200 further includes a micro channel member 40 covering a passivation layer 16. The micro channel member 40 is provided with micro channels (not illustrated) having a micro scale and micro injection holes 401 (illustrated with a dotted line). The micro channels are communicated with holes 161. Accordingly, after the micro channel members 40 are positioned on the passivation layer 16, beads inserted into the micro channels 401 through a reservoir (not illustrated) may be inserted into the holes 161 through the micro injection holes 401. That is, the micro channels 401 include the micro injection holes 401 corresponding to the holes 161, so that the beads may be inserted into the holes 161 through the micro injection holes 401. Further, the beads positioned outside the holes 161 may be removed by a buffer solution. That is, it is possible to remove the beads by injecting the buffer solution between the micro channel members 40 and the passivation layer 16 and washing the beads.

Figure 6:
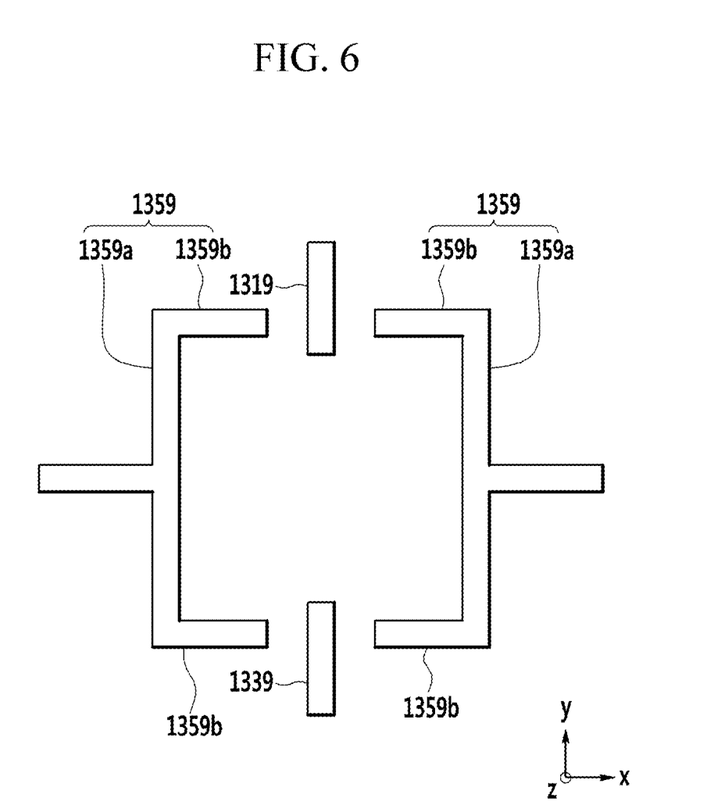
FIG. 6 is a schematic top plan view of electrodes included in a biosensor according to a third exemplary embodiment.

FIG. 6 schematically illustrates a plane structure of electrodes 1319, 1339, and 1359 included in a biosensor according to an exemplary embodiment. The remaining parts, except for the structure of the electrodes of FIG. 6, are similar to those of the structure of the biosensor 100 of FIG. 1, so that a detailed description thereof will be omitted.

As illustrated in FIG. 6, first exposed electrodes 1319 and second exposed electrodes 1339 are spaced apart from each other and linearly formed. That is, each of the first exposed electrodes 1319 and the second exposed electrodes 1339 is positioned while being equally elongated in the y-axis direction. The first exposed electrode 1319 may be a working electrode, and the second exposed electrode 1339 may be a counter electrode. Otherwise, an opposite case may be available. Accordingly, an electric field is formed by a potential difference between the first exposed electrode 1319 and the second exposed electrode 1339 and surrounds beads (not illustrated), so that it is possible to apply an electric field to the beads.

A pair of third exposed electrodes 1359 are reference electrodes, and are operated according to the maintenance of the potential of the first exposed electrode 1319 and the second exposed electrode 1339. A height of the third exposed electrode 1359 may be the same as a height of the first exposed electrode 1319 and the second exposed electrode 1339. The third exposed electrode 1359 may be formed outside the holes separately from the first exposed electrode 1319 and the second exposed electrode 1339, or may be immersed in a liquid and the like and fixed.

As illustrated in FIG. 6, each of the pair of third exposed electrodes 1359 includes exposed electrode parts 1359*a* and 1359*b*. The exposed electrode part 1359*a* is elongated in a direction, that is, the y-axis direction, parallel to a direction, in which the first exposed electrode 1319 is elongated. Further, the pair of exposed electrode parts 1359*b* are connected to both ends of the exposed electrode part 1359*a* while forming a right angle. The pair of exposed electrode parts 1359*b* are elongated toward the first exposed electrode 1319 and the second exposed electrode 1339 while being spaced apart from the first exposed electrode 1319 and the second exposed electrode 1339. A length of the pair of exposed electrode parts 1359*b* is smaller than a length of the exposed electrode part 1359*a*.

Hereinafter, the present invention will be described in more detail through an experimental example. The experimental example is simply for the purpose of illustrating the present invention, and the present invention is not limited thereto.

EXPERIMENTAL EXAMPLE

Biosensor Manufacturing Experiment

A biosensor with a 10×10 array was manufactured. Two electrodes were manufactured by depositing Ti/Pt (10 nm/100 nm) on each sensor part of the biosensor. Further, holes were patterned by using SU-8 so as to capture magnetic beads around the electrodes. A diameter of the patterned hole was about 4 µm and when the magnetic bead having a diameter of about 2.8 µm was used, the biosensor was manufactured so that one to three magnetic beads may be captured at each hole.

In the present experimental example, an experiment for detecting AβO, which is important for early diagnosis of Alzheimer's disease, was conducted. When the AβO is used in the actual experiment, a characteristic thereof is not stable, so that efficiency of the biosensor is verified by using an oligomer mimicking standard protein (OMSP) describing the AβO. The magnetic beads were introduced by using the micro channel members after an antibody, an HRP, and the OMSP for each concentration were incubated externally for about 45 minutes. The introduced magnetic beads were inserted into the holes by using the magnetic body. Further, the magnetic beads positioned outside the holes were removed by making a phosphate buffered saline (PBS) buffer solution flow. Then, impedance was measured by applying a voltage to the biosensor. After the impedance was measured, the magnetic beads were removed by making the PBS buffer solution flow again after removing the magnetic body. Then, a change in impedance for each concentration was observed by inserting the magnetic beads combined with the OMSP with a different concentration again. The remaining experiment processes may be easily understood by those skilled in the art, so that a detailed description thereof will be omitted.

Experimental Result

Figure 7:
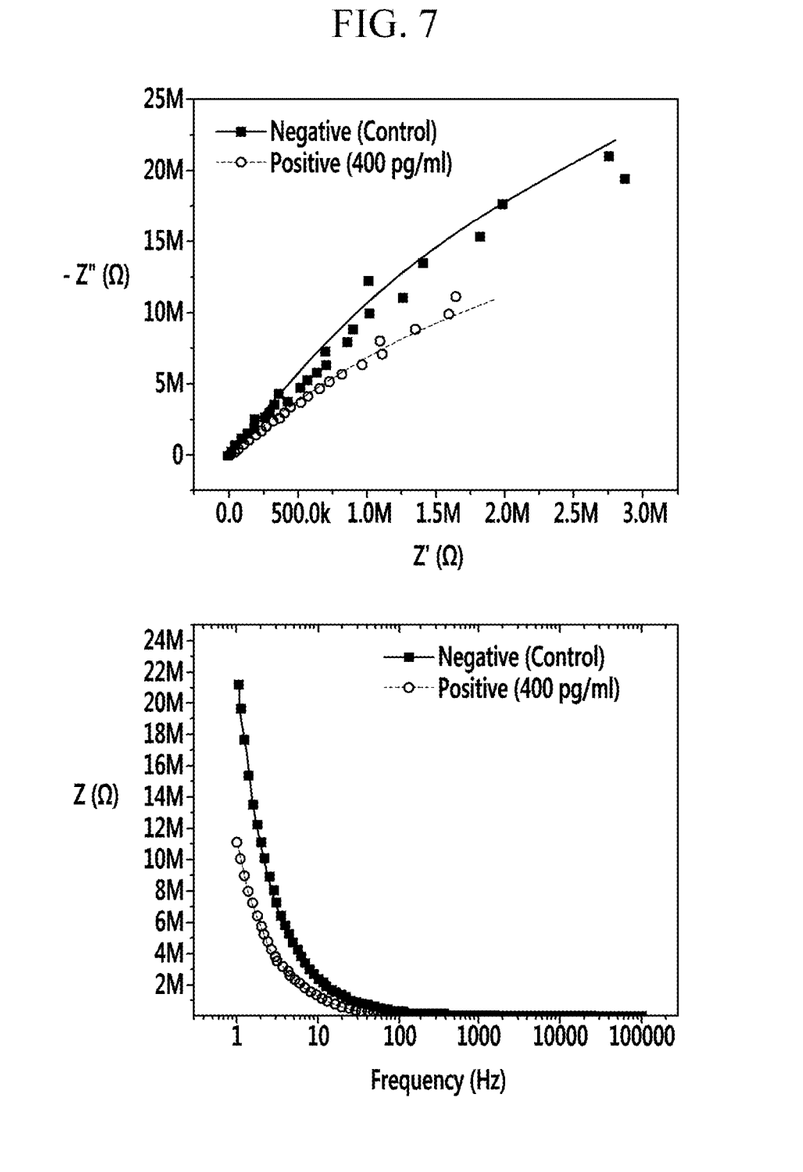
FIG. 7 is a Nyquist diagram and a graph representing impedance in a case where an OMSP is combined with a magnetic bead according to an experimental example and a case where an OMSP is not combined with a magnetic bead as a standard sample.

FIG. 7 represents a Nyquist diagram and impedance in a case where an OMSP is combined with the magnetic bead and a standard sample case where an OMSP is not combined with a magnetic bead. That is, FIG. 7 represents a Nyquist diagram in a case where the OMSP is combined with the magnetic bead and a case where the OMSP is not combined with the magnetic bead as a standard sample at an upper side thereof, and represents a graph of impedance of the cases at a lower side.

As illustrated with a circle shape in FIG. 7, it can be seen that when the OMSP is combined, total impedance is decreased. Particularly, it can be seen that a difference between the two cases at a low frequency is notable. This means that the impedance is considerably changed at a low frequency according to the concentration of the OMSP, and means that conductivity of a surface of the magnetic bead is increased according to the combination of the OMSP.

Figure 8:
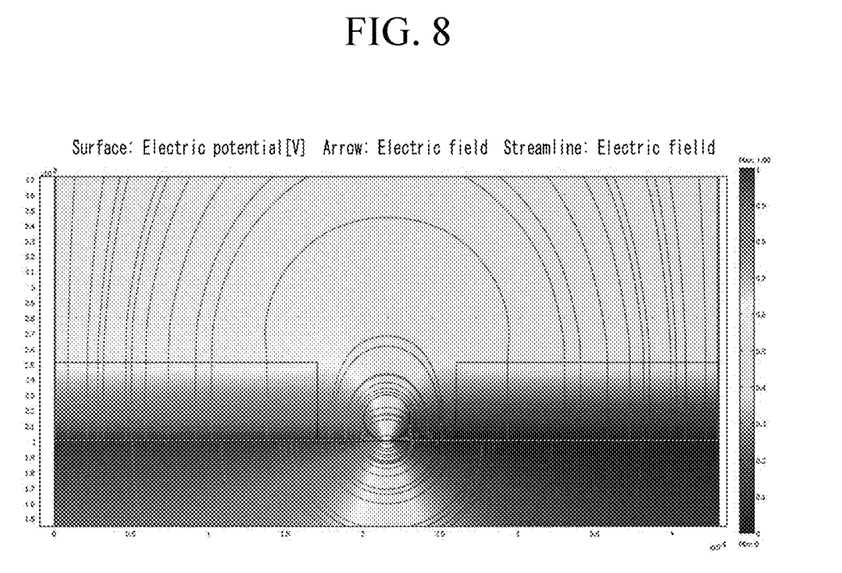
FIG. 8 is a diagram illustrating a result of a simulation through a COMSOL in an electric field direction of a voltage distribution of a two electrode structure according to the experimental example.

FIG. 8 illustrates a result of a simulation through a COMSOL in an electric field direction of a voltage distribution of a two electrode structure.

As illustrated in FIG. 8, it can be seen that a part of an electric field is formed in the magnetic bead, and most of the electric field is formed along the surface of the magnetic bead. When a frequency becomes low, a change in a current by an electric flux line communicated to the outside of the magnetic bead is increased, which means that a low frequency is advantageous when measuring a change in impedance.

Experiment of Concentration Change of OMSP

A change in impedance was measured five times while changing a concentration of OMSP by using the aforementioned biosensor. The remaining experimental processes are the same as the aforementioned contents.

Experimental Result

Figure 9:
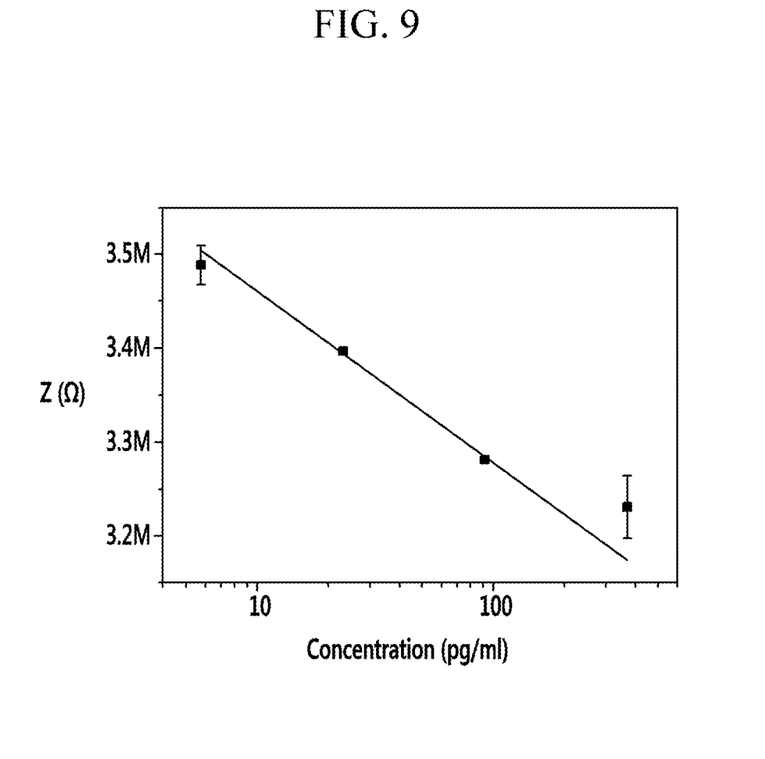
FIG. 9 is a graph of a result of the five-times measurement of impedance change while changing a concentration of OMSP according to the experimental example.

FIG. 9 illustrates a result of the measurement of a change in impedance five times while changing a concentration of OMSP.

As illustrated in FIG. 9, a change in impedance according to a concentration was measured as about 180 kΩ/dec, and it was difficult to distinguish a difference at 1 kHz or more during the measurement. It can be seen that it is possible to detect the antigens to a minimum of about 1 pg/ml or less during the measurement of the OMSP according to a concentration.

It can be seen that it is possible to measure a concentration of the OMSP describing the actual AβO by using the biosensor, which is manufactured as described above. That is, surface conductivity was decreased along the OMSP combined with the magnetic bead, so that it was possible to measure a concentration of the OMSP, which was indirectly confirmed through a distribution of a surface electric field through the COMSOL.

Experiment of Concentration Change of PSA

A prostate specific antigen(PSA) is a protein produced by the prostate gland and is a sensitive biomarker of prostate cancer or other prostate disorders.

The magnetic beads were introduced by using the micro channel members after an anti-PSA antibody, the PSA antigen for each concentration were incubated externally for about 45 minutes. The introduced magnetic beads were inserted into the holes by using the magnetic body. Further, the magnetic beads positioned outside the holes were removed by making a phosphate buffered saline (PBS) buffer solution flow. Then, impedance was measured by applying a voltage to the biosensor. After the impedance was measured, the magnetic beads were removed by making the PBS buffer solution flow again after removing the magnetic body. Then, a change in impedance for each concentration was observed by inserting the magnetic beads combined with the PSA with a different concentration again. The remaining experiment processes may be easily understood by those skilled in the art, so that a detailed description thereof will be omitted.

Experimental Result

Figure 10:
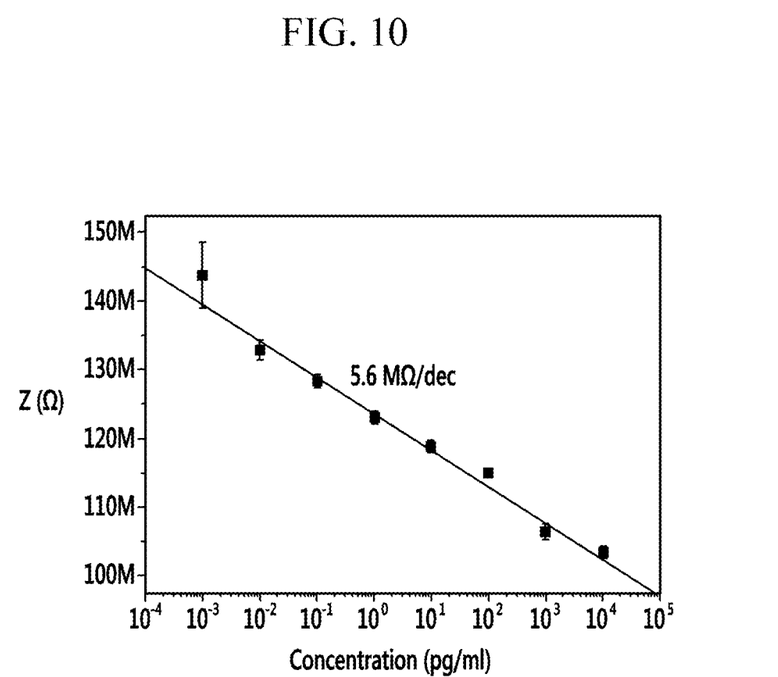
FIG. 10 is a graph of a result of the five-times measurement of impedance change while changing a concentration of Prostate-Specific Antigen (PSA) according to the experimental example.

FIG. 10 is a graph of a result of the five-times measurement of impedance change while changing a concentration of Prostate-Specific Antigen (PSA).

As illustrated in FIG. 10, a change in impedance according to a concentration was measured as about 5.6 MΩ/dec. And its limit of detection was approximately 10 fg/ml, which is comparable to to those of advanced biosensors based on nanotechnology, but BEIS has the advantageous of having a simple fabrication process, low cost, and reusability.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A biosensor, comprising:
a substrate;
an electrode pattern, positioned on the substrate, and comprising a first electrode pattern part and a second electrode pattern part spaced apart from the first electrode pattern part;
a passivation layer made of a material having an electric insulation property, positioned on the electrode pattern, covering the substrate and making a direct contact with the substrate, and comprising holes spaced apart from each other; and
beads positioned at the holes, wherein an entire bottom of each of the holes is sealed off to limit a flow of an element therethrough,
wherein the beads are configured to attach to an antibody,
wherein the first electrode pattern part comprises first exposed electrodes not covered with the passivation layer to be exposed to an outside through the holes, and respectively connected to first branched electrodes covered with the passivation layer,
wherein the second electrode pattern part comprises second exposed electrodes not covered with the passivation layer to be exposed to the outside through the holes, and respectively connected to second branched electrodes covered with the passivation layer,
wherein each hole formed in the passivation layer is configured to capture one bead at a time, and an opening formed in the electrode pattern in direct contact with the substrate positioned within each hole has a width smaller than a diameter of each bead,
wherein the first exposed electrodes and the second exposed electrodes are configured to apply an electric field to the beads by a voltage difference between the first exposed electrodes and the second exposed electrodes, and
wherein an end of each first exposed electrode extends straight to an intermediate portion of each hole to contact a corresponding bead, and an end of each second exposed electrode partially surrounds the corresponding bead.

2. The biosensor of claim 1, wherein a portion of the passivation layer is in direct contact with the substrate, and a height of the portion of the passivation layer in direct contact with the substrate is ⅔ to 5 times the diameter of each bead.

3. The biosensor of claim 1, wherein a part of the passivation layer is in direct contact with the substrate, and a height of the part of the passivation layer in direct contact with the substrate is 3 to 20 times the diameter of each bead, and the diameter of each bead is 1 μm or less.

4. The biosensor of claim 1, wherein the end of each first exposed electrode is linear, and the end of each second exposed electrode is curved.

5. The biosensor of claim 4, wherein a voltage is applied to the first electrode pattern part, and the second electrode pattern part is grounded.

6. The biosensor of claim 1,
wherein the first electrode pattern part comprises:
a first main electrode extending in a first direction,
first auxiliary electrodes spaced apart from each other, connected to the first main electrode, and extending in a second direction different from the first direction,
first reaction electrodes respectively connected to the first auxiliary electrodes, and extending in the first direction, and the first branched electrodes respectively connected to the first reaction electrodes and extending in the second direction, wherein the second electrode pattern part comprises:
a second main electrode spaced apart from the first main electrode, and extending in the first direction;
second auxiliary electrodes spaced apart from each other, connected to the second main electrode, and extending in the second direction and alternately positioned with the first auxiliary electrodes;
second reaction electrodes respectively connected to the second auxiliary electrodes, and extending in the first direction, and
the second branched electrodes respectively connected to the second reaction electrodes and extending in the second direction.

7. The biosensor of claim 6, wherein each first branched electrode is connected to at least one first exposed electrode, and each second branched electrode is connected to at least one second exposed electrode.

8. The biosensor of claim 1, further comprising a micro channel member covering the passivation layer,
wherein the micro channel member comprises micro injection holes in communication with the holes.

9. The biosensor of claim 1, further comprising a magnetic body positioned under the substrate,
wherein the magnetic body is freely movable under the substrate, and
wherein each bead is magnetic.

10. The biosensor of claim 1, wherein the end of each second exposed electrode partially surrounding each bead is spaced apart from each bead.

* * * * *